United States Patent [19]

Leighton

[11] Patent Number: 4,831,160

[45] Date of Patent: May 16, 1989

[54] REMOVAL OF VOLATILE ACIDS FROM NMP SOLVENT VAPORS WITH SACRIFICIAL METAL AND ION EXCHANGE

[75] Inventor: Milton D. Leighton, Florham Park, N.J.

[73] Assignee: Exxon Research and Engineering Company, Florham Park, N.J.

[21] Appl. No.: 416

[22] Filed: Jan. 5, 1987

[51] Int. Cl.$^4$ ................. C07D 201/00; C07D 207/267
[52] U.S. Cl. .................................................. 548/555
[58] Field of Search ........................................ 548/555

[56] References Cited

U.S. PATENT DOCUMENTS

| | | | |
|---|---|---|---|
| 2,316,931 | 4/1943 | Brandt | 196/58 |
| 2,846,354 | 8/1958 | Holm et al. | 196/14.42 |
| 3,531,538 | 9/1970 | Duerksen et al. | 260/674 |
| 3,980,449 | 9/1976 | Zetlmeisl, et al. | 44/68 |
| 4,294,689 | 10/1981 | Sequeira et al. | 208/326 |
| 4,297,150 | 10/1981 | Foster et al. | 148/6.3 |
| 4,396,492 | 8/1983 | Bardasz | 208/47 |
| 4,490,240 | 12/1984 | Comeaux et al. | 208/47 |

FOREIGN PATENT DOCUMENTS 867276  3/1971  Canada ..................................... 31/68
2088850  6/1982  United Kingdom .

OTHER PUBLICATIONS

"Metallic Preparation for Stabilizing the Lubricating and Anti-Corrosion Action of Oils", Barannik, et al., Zashch Met. 1976 12(3) 336–339 (abstract).
"Stability and Corrosion Activity of Dichloromethanes", Borisova, Mater, Korroz Svarka 1975, 162–166 (abstract).
Encyclopedia of Chemical Technology, 3rd Ed., vol. 14, pp. 573–575.

*Primary Examiner*—David B. Springer
*Attorney, Agent, or Firm*—Joseph J. Allocca

[57] ABSTRACT

Volatile acids present in n-methyl pyrrolidone vapor from solvent extraction processes can be reacted with sacrificial metals such as magnesium to concentrate the acid salts into a small volume of oil/NMP. Steam stripping removes NMP from the oil/NMP mixture while simultaneously springing a portion of the light carboxylic acids from their salts, the acids going with the NMP. This condensed NMP stream containing the light carboxylic acids is contacted with an ion exchange resin which removes the acids from the NMP. The purified small volume of NMP is returned to the extraction process.

3 Claims, 1 Drawing Sheet

REMOVAL OF VOLATILE ACIDS FROM NMP SOLVENT VAPORS WITH SACRIFICIAL METAL AND ION EXCHANGE

BACKGROUND OF THE INVENTION

Hydrocarbon oils used to produce high value products such as lubricating oils, turbine oils, white oils, refrigerator oils and other specialty oils are subjected to numerous treating processes including distillation, vacuum distillation, dewaxing, extraction, etc. in order to produce the final desired products.

Extraction is practiced so as to remove undesirable materials from the oils. The undesirable materials are aromatics and polar compounds which are detrimental to the stability of the oil.

Extraction processes utilizing n-methyl-2-pyrrolidone have been found to produce oils of extremely satisfactory make-up. The process, however, is marked by the extraction plant itself being susceptible to corrosion duet to the acidic components present in the oil which over time become concentrated in the NMP solvent or to acidic components inadvertently introduced into the NMP from other sources, such as cooling water leaks, etc.

To overcome the corrosion problem, various solutions have been offered.

GB No. 2,088,850 teaches that the acids and/or chloride contaminants present in NMP can be removed using basic ion-exchange resins. The acid and/or chloride contaminant level can be kept low by continuous or semi-continuous treatment. The entire volume of NMP is contacted with the ion exchange resin.

U.S. Pat. No. 4,490,240 teaches that plant corrosion can be reduced by contacting the NMP streams with a sacrificial metal which metal possesses an electrochemical potential higher than that of the metal used in the construction of the process equipment. In this way the contaminants are converted into non-corrosive species which can pass harmlessly through the plant or be removed in the extract product.

THE PRESENT INVENTION

The present invention reduces or eliminates extraction plant corrosion by a process whereby NMP vapor is contacted with a sacrificial metal bed to convert the corrodents to acid salts which under a reflux of NMP becomes concentrated in a small volume of NMP and oil. The small volume of NMP/oil/acid salt is then subject to steam stripping to remove the NMP from the mixture. Steam stripping not only springs the NMP from the mixture, it also converts some of the acid salts of the lower carboxylic acids back into the acid form and these acids are concentrated in the small volume of recovered NMP. This small volume of condensed NMP and acids is then contacted with an ion-exchange resin which removes the acid contaminant from the NMP. Removing the light carboxylic acids from the NMP and not simply letting them remain in the recycled NMP reduces the quantity of sacrificial metal which needs to be made available over the course of time.

This invention obtains a beneficial effect by: removing the light extract oil from the recovered NMP, thus reducing treat required in the extraction tower; removing all the volatile acids from the NMP, thus reducing carbon steel corrosion to essentially nil; concentrating the sacrificial metal salts into a small volume extract oil stream that can be sent to fuel oil, thus not incurring a debit due to FCCU catalyst poisoning; and selectively remove the $C_1$-$C_4$ carboxylic acids from the system which in turn reduces the amount of sacrificial metal required to keep the vigil to remove the volatile acids which also further reduces disposal of sacrificial salts.

The present invention is directed to a method for reducing NMP extraction plant corrosion, which method comprises:

(a) passing the extract solution stream from an extraction zone to a separation zone, such as to a high pressure flash tower, wherein the extraction stream is separated into an NMP-rich vapor stream and an extract oil concentrate stream;

(b) passing the NMP-rich vapor stream to a sacrificial metal bed contactor wherein the contaminants are removed from the NMP by conversion into metal salts and acid salts, which concentrate in a bottoms fraction consisting of liquid NMP, residual oil, metal salts and acid salt, the purified NMP being recovered as overhead vapor;

(c) passing the bottoms fraction to a steam stripper which separates the fraction into (1) a light extract oil/metal salt fraction, and (2) an NMP fraction which contains organic acids resulting from the hydrolysis of the acid salts; and (d) passing the NMP/light acids fraction to an ion exchange resin bed wherein the acids are removed from the NMP, yielding a pure stream of NMP suitable for recycle.

In the process of the present invention, the sacrificial metal is any metal which more easily reacts with the corrodents than do the materials used in plant construction, i.e. sacrificial metals are those with higher electrochemical potentials than the metals used in plant construction. Such sacrificial metals include magnesium, zinc, calcium, barium, strontium and mixtures thereof, preferably magnesium. These metals may be used in any convenient form including blocks, brushes, chips, shavings, donuts, ribbons, sponges, filings, beads, nodules, sheets, etc. Ion exchange resins employed are typically basic resins, which are commercially available materials. Suitable resins are Amberlyst series materials, i.e., Amberlyst A21. Spent resin beds may be regenerated using any of the well known procedures, e.g. washing with caustic soda solutions, etc.

Figure 1:
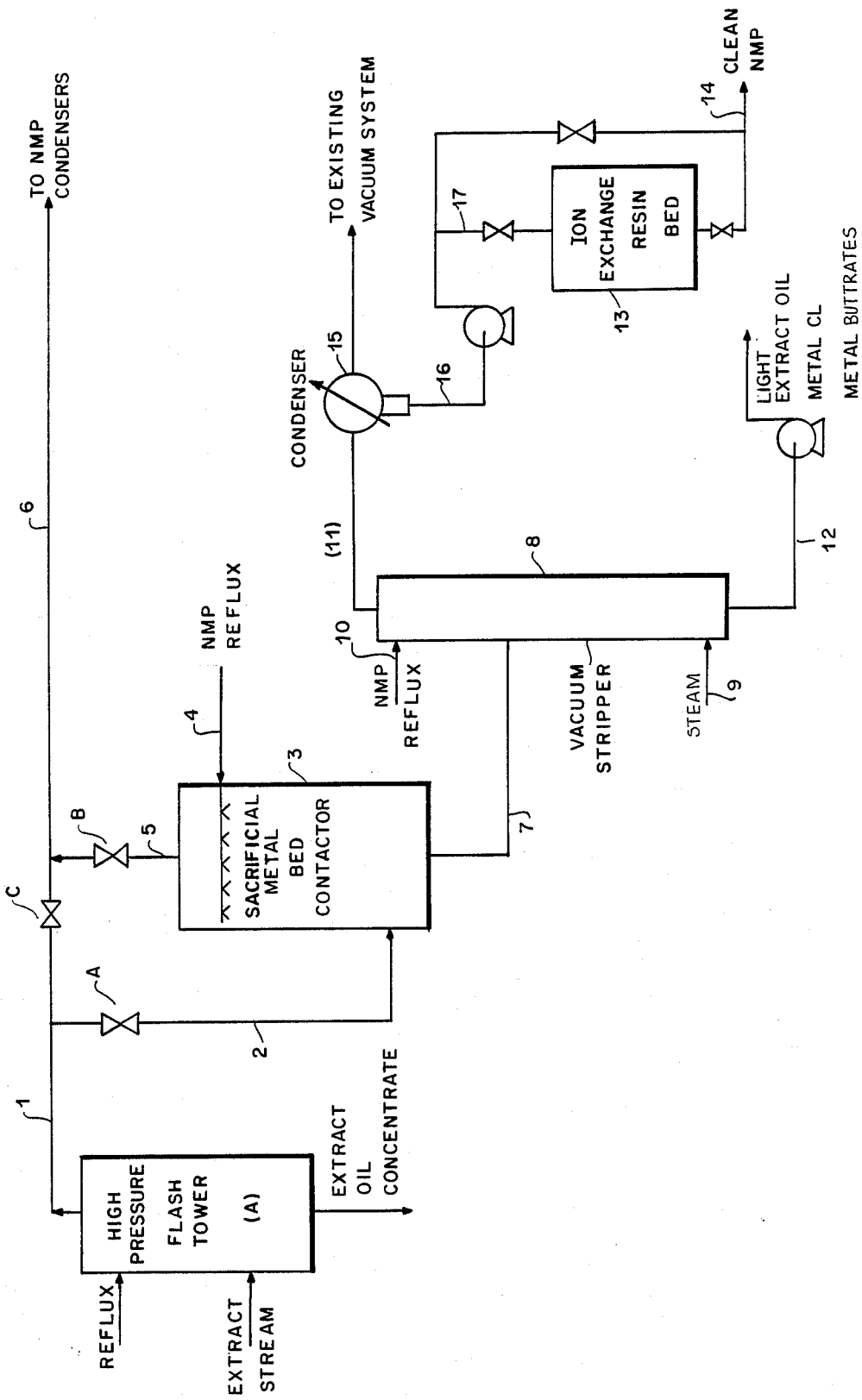
FIG. 1 is a schematic of the process of the present invention.

NMP vapors at from 250° F. to 650° F., preferably about 400° to 600° F., from the high pressure flash tower (A) of the extract recovery zone is passed via line 1 to line 2 and then into the sacrificial metal bed contactor (3) for the sake of simplicity the sacrificial metal is identified as magnesium. NMP reflux is fed via line 4 into contactor 3. Substantially all of the NMP vapor in purified form is recovered overhead via line 5 and is sent to NMP condensers (not shown) via line 6. During the period of Mg bed replacement valves A and B can be closed and valve C opened to bypass the sacrificial metal bed and the NMP vapor fed directly to the condenser.

A small volume mixed stream of NMP/oil/acid salts is recovered from the contactor 3 via line 7 and is sent via line 7 to vacuum steam stripper 8. Steam is introduced via line 9 and NMP reflux via line 10. NMP is stripped from the mixture in stripper 8 and is recovered as overhead via line 11. Stripper 8 is preferably a dedicated stripper used only for this particular application. In stripper 8 the steam converts a portion of the carboxylic acid salts back into the volatile acid form and the acids leave with the NMP via line 11. A light oil is recovered via line 12. This light oil contains the balance of the unconverted acid salts and the metal hydroxide from which the volatile acid was sprung, as well as the sacrificial metal salts. The mixture of NMP and light carboxylic acids is fed via line 11 to condenser 15 and the condensed liquid NMP and carboxylic acid is fed via lines 16 and 17 into ion exchange vessel 13 wherein the light carboxylic acids are adsorbed and a stream of clean NMP is produced, this clean NMP being recovered for recycle via line 14.

Thus, all of the NMP vapors from the high pressure flash tower are contacted with the sacrificial metal bed and substantially all leave the bed clean of volatile acids and oil. A small volume of light extract oil is condensed by the NMP reflux in the sacrificial metal bed and carries the salts of the sacrificial metal and of the carboxylic acids over to the vacuum steam stripper. The amount of this oil stream can be controlled by controlling the amount of refluxing practiced in the high pressure flash tower (A). Since the sacrificial metal bed is employed after the HP flash tower, it is operating on a substantially oil-free NMP stream and, consequently, only a small stream of condensed oil and acid salt contaminants is recovered from the sacrificial metal bed. Conversely, if the sacrificial metal bed were in the HP flash tower, all the salts would go with the substantially larger volume of extract oil concentrate coming from the HP flash tower which is subsequently sent to a steam stripper wherein a significantly larger volume of NMP is recovered, which would be contaminated with regenerated carboxylic acids. This larger volume presents either or both handling problems (for clean-up) or the volume is simply recycled to the main NMP inventory. The practice of the present invention avoids these problems.

What is claimed is:

1. A method for reducing the concentration of acidic components in the N-methyl-pyrrolidone (NMP) used in extraction plants and thereby reducing NMP extraction plant corrosion, which method comprises:
   (a) passing the extract stream from an extraction zone to a separation zone wherein the extraction steam is separated into an NMP-rich vapor and an extract oil concentrate stream;
   (b) passing the NMP rich vapor stream to a sacrificial metal bed contactor containing a metal having a higher electrochemical potential than the metals used in the construction of the extraction plant wherein the acidic component contaminants are removed from the NMP by conversion into metal salts of the acidic contaminants which under a reflux of NMP concentrate into a bottom fraction consisting of liquid NMP, residual oil, and the metal salts of the acidic contaminants, the purified NMP being recovered as overhead vapor;
   (c) passing the bottoms fraction to a steam stripper which separates the fraction into light extract oil/metal salt fraction and a vapor NMP fraction which contains organic acids resulting from the hydrolysis of a portion of the metal salts
   (d) passing the NMP volatile acids fraction after condensing to a liquid to an ion exchange resin bed wherein the acids are removed from the NMP, yielding a pure stream of NMP suitable for recycle.

2. The method of claim 1 wherein the sacrificial metal is magnesium, zinc, calcium, barium, strontium or mixtures thereof.

3. The method of claim 1 wherein the ion exchange resin is a basic resin.

* * * * *